US007049340B1

(12) United States Patent
Rekik

(10) Patent No.: US 7,049,340 B1
(45) Date of Patent: May 23, 2006

(54) NEUROPROTECTIVE AND RETINOPROTECTIVE OPHTHALMOLOGIC DRUGS

(76) Inventor: Raouf Rekik, 3 avenue Louis Brailles, 1002 Tunis (TN)

( * ) Notice: Subject to any disclaimer, the term of this patent is extended or adjusted under 35 U.S.C. 154(b) by 272 days.

(21) Appl. No.: 10/018,235

(22) PCT Filed: Jun. 16, 2000

(86) PCT No.: PCT/FR00/01679

§ 371 (c)(1),
(2), (4) Date: May 22, 2002

(87) PCT Pub. No.: WO00/76499

PCT Pub. Date: Dec. 21, 2000

(30) Foreign Application Priority Data

Jun. 16, 1999 (TN) ............................. SN 99 122
Dec. 6, 1999 (FR) ............................. 99 15359

(51) Int. Cl.
*A61K 31/215* (2006.01)
(52) U.S. Cl. .......................... 514/530; 514/912
(58) Field of Classification Search ................ 514/530
See application file for complete search history.

(56) References Cited

FOREIGN PATENT DOCUMENTS

| EP | 0 114 333 A2 | 12/1983 |
| EP | 0 158 157 A1 | 3/1985 |
| EP | 0 220 107 A2 | 10/1986 |
| WO | WO 99/36062 | 7/1999 |

OTHER PUBLICATIONS

H.P. Chase et al, "Angiotensin-converting enzyme inhibitor treatment for young normotensive diabetic subjects: a two-year trial", Annals of ophthalmology, (Aug. 1993) 25 (8) pp. 284-289.*
Bunning "Inhibition of Angiotensin Converting Enzyme by 2-[N-[(S)-1-carboxy-3-penoxy]-L-alanyl]-(1S,3S,5S)-2-azabicyclo[3.3.0]octaine-3-carboxylic acid (HOE 498 Diacid) Comparison with Captopril and Enalaprilat", Arzneim-Forsch./Drug Research, 34;1406-1410; (1984).
Database WPI Section Ch, Week 199401, "Peptides of Formulae Gly-His-Phe (I) and Tyr-Arg-Pro-Tyr (II) Inhibit Angiotensin I Converting Enzyme (ACE)", Derwent Publication Ltd., London, GB; Class B03, AN 1994-002154 XP002157734.
Detry-Morel, "Perspectives in the Medical Treatment of Glaucomatous Neuropathy Bases for Neuroprotection", J. Fr. Ophtmalmol., 22(1):122-134; (1999) XP-00087-144 (translation attached).
Garg et al., "Renal and Retinal Changes after Treatment with Ramipril and Pentoxifyline in Subjects with IDDM", Ann. Ophthalmol., 30(1):33-37; (1998) XP-000980142.
Shah et al., "Ocular Hypotensive Effect of Ramiprilat in Chronic and Acute Models of Glaucoma in Rabbits", Indian Journal of Pharmacology, 31:110-115; (1999) XP-00980134.
Kulshrestha et al., "Protective Effect of Angiotensin Converting Enzyme Inhibitors in Diabetic Retinopathy", IVOS, 40(4):312; (1999) XP-00980128.
Kusaka-Nakamura et al., "Antihypertensive Treatment in Spontaneously Hypertensive Rats with Streptozotocin-Induced Diabetes Mellitus", Acta Physiol. Hung. 71(2):251-269; (1988) XP-000980228.
Vasmant et al., "Renin-Angioistensin System and A New Converting Enzyme Inhibitor", J. of Cardiovascular Pharmacology 14 (suppl. 4): 546-552; (1989).
Vogh et al., "Effects of Inhibition of Angiotensin Converting Enzyme and Carbonic Anhydrase on Fluid Production by Ciliary Process, Choroid Plexus, and Pancreas", J. of Ocular Pharmacology 5(4);303-311; (1989) XP-00980132.
Yamagami et al., "Captopril", Dept. of Ophthalmology, Hirosaki Univ. School of Med., 34:290-297; (1983) XP-000980116.
Holman et al., "Efficacy of atenolol and captopril in reducing risk of macrovascular and microvascular complications in type 2 diabetes: UKPDS 39," BMJ 317:713-720 (1998).

* cited by examiner

Primary Examiner—Kevin E. Weddington
(74) Attorney, Agent, or Firm—Clark & Elbing LLP

(57) ABSTRACT

The invention concerns a neuroprotective and retinoprotective medicine, whereof the active principle is selected among a group of compounds consisting of ramipril, ramiprilat or any other ramiprilat derivative capable of releasing it in the organism whereto it is administered. Said medicine is used for prevention, or even for improving visual acuity and visual field in normal subjects, as well as for treating ophthalmologic pathologies involving a vascular factor, in particular glaucomatous neuropathy, degenerative choriopathy of strong myopia, age-related maculopathy, serous central chorioretinopathy, hereditary dystrophy of the retina and retinal venous occlusions. It almost invariably improves the visual function (acuity and visual field).

19 Claims, 17 Drawing Sheets

NEUROPROTECTIVE AND RETINOPROTECTIVE OPHTHALMOLOGIC DRUGS

Figure 1:
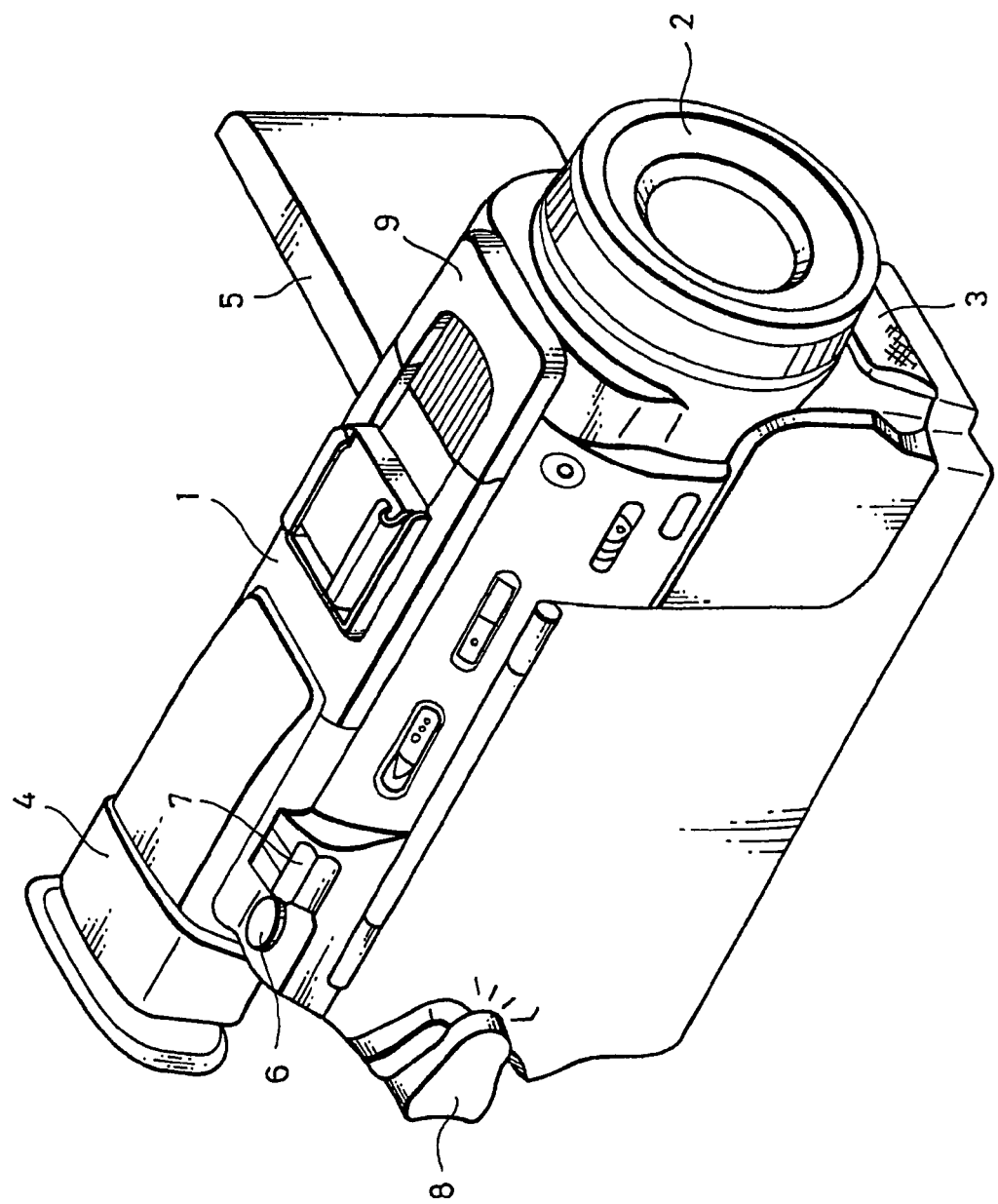

This application claims the benefit of foreign priority under 35 U.S.C. § 119 to applications FR 99/15359, filed Dec. 16, 1999, and SN 99 122, filed Jun. 16, 1999. This application is a 371 of PCT/FR00/01679, filed Jun. 16, 2000.

The invention relates to the production of neuroprotective and retinoprotective drugs for maintaining or improving visual function (visual acuity and field of vision). More particularly, it relates to such drugs for the treatment of ophtalmologic disorders involving chorioretinal deterioration or deterioration of the optic nerve or both at once, with a resultant progressive loss of vision (visual acuity and field of vision).

Such effects on vision are observed in particular in glaucoma, conventionally associated with the notion of ocular hypertension.

Clearly, ocular hypertension can have a deleterious effect on the optic nerve. However, experience has shown that such a result of intraocular pressure is not necessarily the cause of glaucoma, since it has been observed that many patients suffer from intraocular hypertension without running any risk of degradation of the optic nerve or of a progressive reduction in their field of vision. In contrast, attacks of a glaucomatous nature on the optic nerve have been observed in other categories of patients, associated with a progressive loss of field of vision, with no concomitant increase in intraocular pressure.

Of course, some prior art documents have already evaluated the presumed action of angiotensin converting enzyme inhibitors (CEI) on ocular pressure (IOP). They did not reveal their importance in improving vision. Further, the recent article by M. Détry Morel published in the review J. Fr. Opthamlol., 1999; 22,1,122–134 (1999), entitled "Perspectives dans le traitement médical de la neuropathie glaucomateuse—Bases de la neuroprotection" [Perspectives in the medical treatment of glaucomatous neuropathy—Bases for neuroprotection], which reviews the current state of the development of drugs for the medical treatment of glaucomatous neuropathies, makes reference to the envisaged use of some vasoactive drugs using certain angiotensin converting enzyme inhibitors for overcoming the reduction in ocular blood flow that can be observed in patients with certain forms of glaucoma. However, according to Détry-Morel, while certain of those drugs are capable of inducing an increase in ocular blood flow, great caution has to be exercised since it is not known whether the increase is accompanied by a beneficial effect for patients or, in contrast, consists solely of a secondary effect. Détry-Morel particularly mentions the possibility that the increase, normally coped with by healthy tissue, may have disastrous consequences in tissue where the vascular bed is initially in a precarious state. Finally, Détry-Morel makes no observations regarding interruption of the optic nerve deterioration process or of the progressive loss of field of vision, and also no mention of an improvement in field of vision for any of the treatments reviewed.

The invention aims to provide drugs intended for the treatment of ophtalmological diseases that can improve visual function, in particular field of vision and visual acuity, in patients suffering from neuropathies such as glaucoma, but also other chorioretinal disorders or deteriorations of the optic nerve that may involve a vascular factor. Examples of these diseases that can be mentioned are:

(1) glaucomatous neuropathies, including glaucoma itself, of course;
(2) degenerative chorioretinopathy in severe myopia;
(3) age-related macular degeneration (ARMD);
(4) diffuse retinal epitheliopathies (DR) and central serous retinopathy (CSCR);
(5) hereditary dystrophies of the retina;
(6) retinal venous occlusions.

The invention is founded on the discovery that when used to treat patients, certain angiotensin I to angiotensin II converting enzyme inhibitors (CEI) cause not only an interruption, which until now has not been observed in patients treated for diseases of the types mentioned above, but moreover at least partial inversion of the visual function degradation process, with an improvement in visual acuity and field of vision.

However, the drugs of the invention are not limited to applications of the type mentioned above. They can usefully be employed to prevent or slow down or even stop "natural" reductions in visual acuity, field of vision or both at once. In particular, they have a happy application in preventing and even reversing visual decline in old age.

Mean retinal sensitivity reduces linearly with age. This decline starts very early on, from 20 years of age and accelerates after the age of 60. In particular, the mean sensitivity (MS) expressed in decibels (dB) obeys the following equation, according to Jaffe:

$$MS(dB) = 28.8 - 0.074 \times age.$$

This is used by the automatic perimeter (octopus™) to calculate age-corrected sensitivity. In the central 30°, retinal sensitivity not only declines faster at the periphery than at the centre, but also more at the upper periphery than in the other quadrants.

Automated perimetry has shown that administering a suitable CEI, in particular ramipril, to normal subjects improves mean sensitivity by more than 1 to 2 dB. The mean sensitivity is that considered to be normal by the software; it includes an evaluation of "normal" losses which is a function of the age of the subjects for whom any losses that are supplemental to the mean sensitivity are to be determined if they suffer from one of the diseases mentioned above, for example.

Currently, the most effective molecule is constituted by ramipril, which has the following formula:

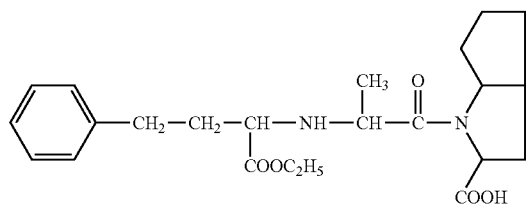

or ramiprilat, which results from de-esterification of ramipril, which has the following formula:

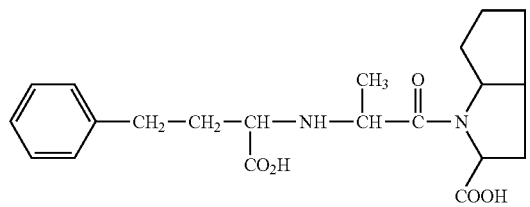

Doubtless, such drugs intervene in the CEI action mechanism, in that they act by preventing the transformation of angiotensin I to angiotensin II (vasoconstrictor) and the degradation of bradykinins (vasodilators). These CEIs thus cause vasodilation, which is exerted on arteries and on veins. Thus, they are mixed vasodilators. It should be remembered that the mechanism for the formation of the bond that can be formed between the inhibitor and the enzyme normally occurs in two phases, the first consisting of the formation of an inhibitor-enzyme complex by a competitive bond, which involves a reaction governed by a constant $K_1$, and the second, consisting of a slow isomerisation of the inhibitor-enzyme complex, itself also governed by a reversible rate constant for this reaction, $k_4$.

An explanation of the above concepts can be found in the publication by D. Vasmant and N. Bender entitled "Renin-angiotensin and ramipril system, a novel converting enzyme inhibitor" in the Journal of Cardiovascular Pathology 14 (suppl. 4) (1989): S49–S56, Raven Press, which itself refers to earlier publications by Büinning P "Inhibition of angiotensin converting enzyme by 2-(N—((S)-1-carboxy-3-phenoxy)-L-alanyl)-(1S,3S,5S)-2azabicyclo(3.3.0)octane-3-carboxylic acid (HOE A98) diacid. Comparison with captopril and enalaprilat" in Drug Research 1984; 34:1406–1410, and the doctoral thesis by Shapiro R. (Ph.D. Thesis, Harvard University Cambridge, Mass., 1983 "Activation and inactivation of rabbit pulmonary angiotensin converting enzyme".

Ramipril and ramiprilat are of particular importance. Ramiprilat, which results from the de-esterification of ramipril, can form more stable complexes with angiotensin converting enzyme than other inhibitors. In particular, the half-life of such complexes is of the order of 12 to 17 hours. They are also distinguished from many other angiotensin converting enzyme inhibitors by their lipophilic nature and by the greater stability of the enzyme-inhibitor couples formed. All of those properties contribute to the manifestation of effects that can be obtained at very small doses, as will be shown in the examples below.

Effective doses for producing effects in the ophtalmologic field are desirably lower than doses that would induce general arterial hypotension in a subject with normal pressure. Clearly, the doses that can be used can be higher in subjects with hypertension, although this is not necessary, since the desired effect is that obtained in the ophtalmologic field.

Clearly, any other CEI with a somewhat lipophilic nature (and, if necessary, retaining a partially hydrophilic nature) can be used instead of ramipril or ramiprilat, that CEI having a high affinity for the converting enzyme and, as a result, allowing the formation of stable enzyme-inhibitor complexes. Complex stability appears to play an important role in the capacity of the drugs in question to exert its visual function improvement action. The invention thus concerns a method of manufacturing a drug for the production of neuroprotective and retinoprotective drugs employing, as the active principle, an angiotensin converting enzyme inhibitor that can form a complex with the angiotensin converting enzyme that is sufficiently stable not only to interrupt the visual function degradation process in patients suffering from the pathologies in question, but also to reverse or regress that process.

In particular, any CEI simultaneously exhibiting the following can be used:
  an equilibrium inhibition constant K, that governs the in vitro inhibition of rabbit converting enzyme by the CEI in question, the constant being lower than that of enalaprilat (50 pmol/l); and
  a constant $k_4$ for the reversible isomerisation of the enzyme-inhibitor complex formed, the constant being lower than that of enalaprilat $(1.1 \times 10^{-4})(S1)$ in a medium (50 mM/l Hepes, 300 mmol/l NaCl, 1 micromol/l $ZnCl_2$, pH 7.5) using Bünning and Shapiro methods under the conditions described by those authors in the articles identified above.

Advantageously again, the CEIs that can be used in the context of the invention have a lipophilic nature that is greater than that of enalaprilat, for example under conditions using comparative measurements of partition coefficients in an octanol/water medium at an acidic pH. The most lipophilic nature will be demonstrated by passage of a larger proportion of the CEI of the invention into the octanol phase than for enalaprilat over a substantial range of acidic pHs, in particular in the range pH 2–4.

When used instead of ramipril, enalaprilat exhibits a moderate improvement in visual function in treated patients. However, the effects observed with ramiprilat, in which the constant $K_i$ is 7 (7 times higher than with enalaprilat) and the constant $k_4$ is $1.8 \times 10^{-5}$ (i.e., the complex that ramiprilat forms with the enzyme is six times more stable than that formed by enalaprilat) are incomparably better. It should be remembered that the physico-chemical indications described above originate from the article by Vasmant et al., loc. cit.

Similar observations based on real trials have not only been carried out on those with glaucomatous neuropathies, but also on those suffering from all other types of disorders involving a vascular factor.

More particularly, the invention concerns the use of the compounds described above for the manufacture of drugs for use in inducing an improvement in visual acuity and field of vision in treated persons.

The invention also concerns pharmaceutical compositions in which the active principles described above are associated with pharmaceutically acceptable vehicles allowing their administration in different forms, in particular: oral forms, parenteral forms, intravenous forms, intramuscular and transdermal forms, and topical forms, in particular as eye or ophthalmic solutions.

While the numerical indications given below should not be considered to be limiting in nature, as those can be left to the clinician and the patient, the following daily doses of active principle—in particular when that active principle is constituted by ramipril or ramiprilat—are effective when administered orally, namely in an amount of 0.5 to 5, preferably 1 to 2 mg/day, for example 1.25 mg/day. Clearly, the dosage can vary from one patient to another and fine tuning can be left to the clinician. These doses may be different when using different drugs. While the following parameter should not be considered to be limiting in nature, it appears that the degree of stability of the complex formed by the selected CEI with the converting enzyme must also be taken into account when determining the most effective daily doses.

There is clear preference for topical forms of administration, in particular for eye or ophthalmic solutions. These have proven to be particularly effective. Eye solutions actually fill a gap in the treatment of opthalmologic diseases that involve a vascular factor and which have not been able to be effectively treated until now.

In other words, in the preferred forms of the drug according to the inventor, the different CEIs used are associated with pharmaceutical vehicles that allow their clinical application in the form of eye lotions.

The invention will now be illustrated by the following description of clinical examples which, of course, are not limiting in nature. In these examples the active principle, in particular ramipril, was administered continuously in an oral form, in an amount of 1.25 mg per day. Reference is also made to the accompanying FIGS. 1 to 8, which indicate the results obtained with an automatic parameter (octopus™) and which demonstrate the capacity of the drugs of the invention to cause a substantial improvement in the field of vision of certain of these patients.

Figure 2:
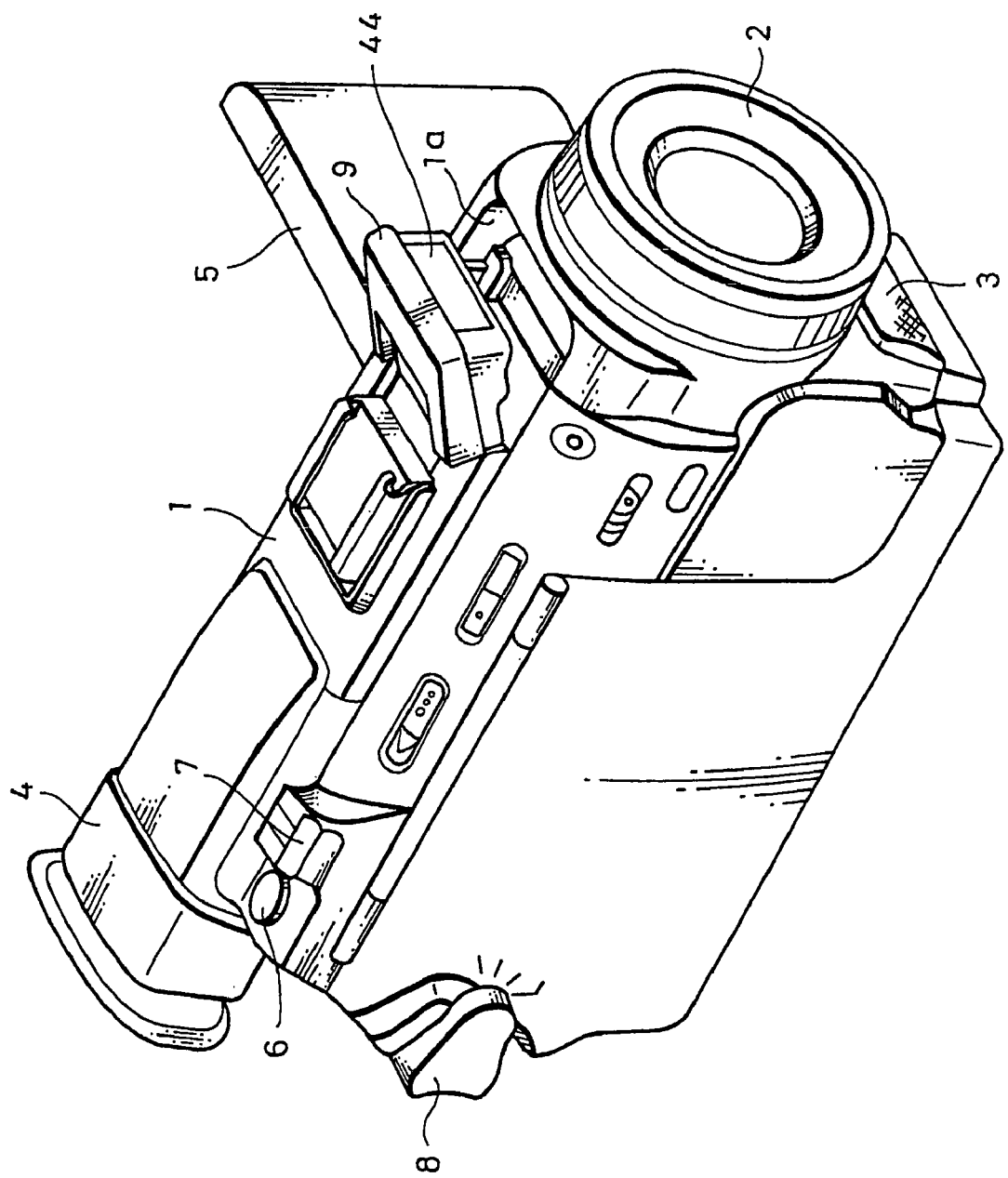
Figure 3:
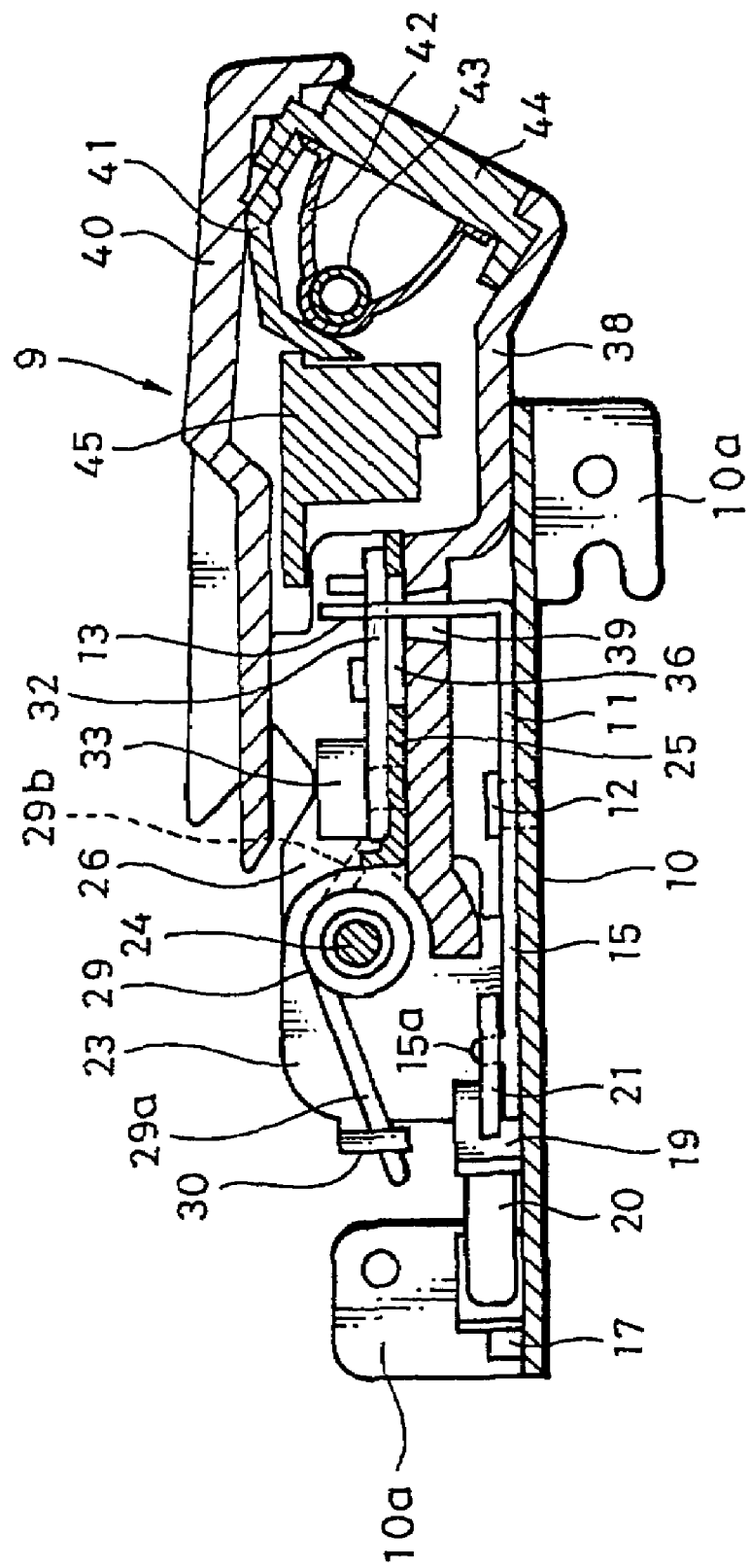
Figure 4:
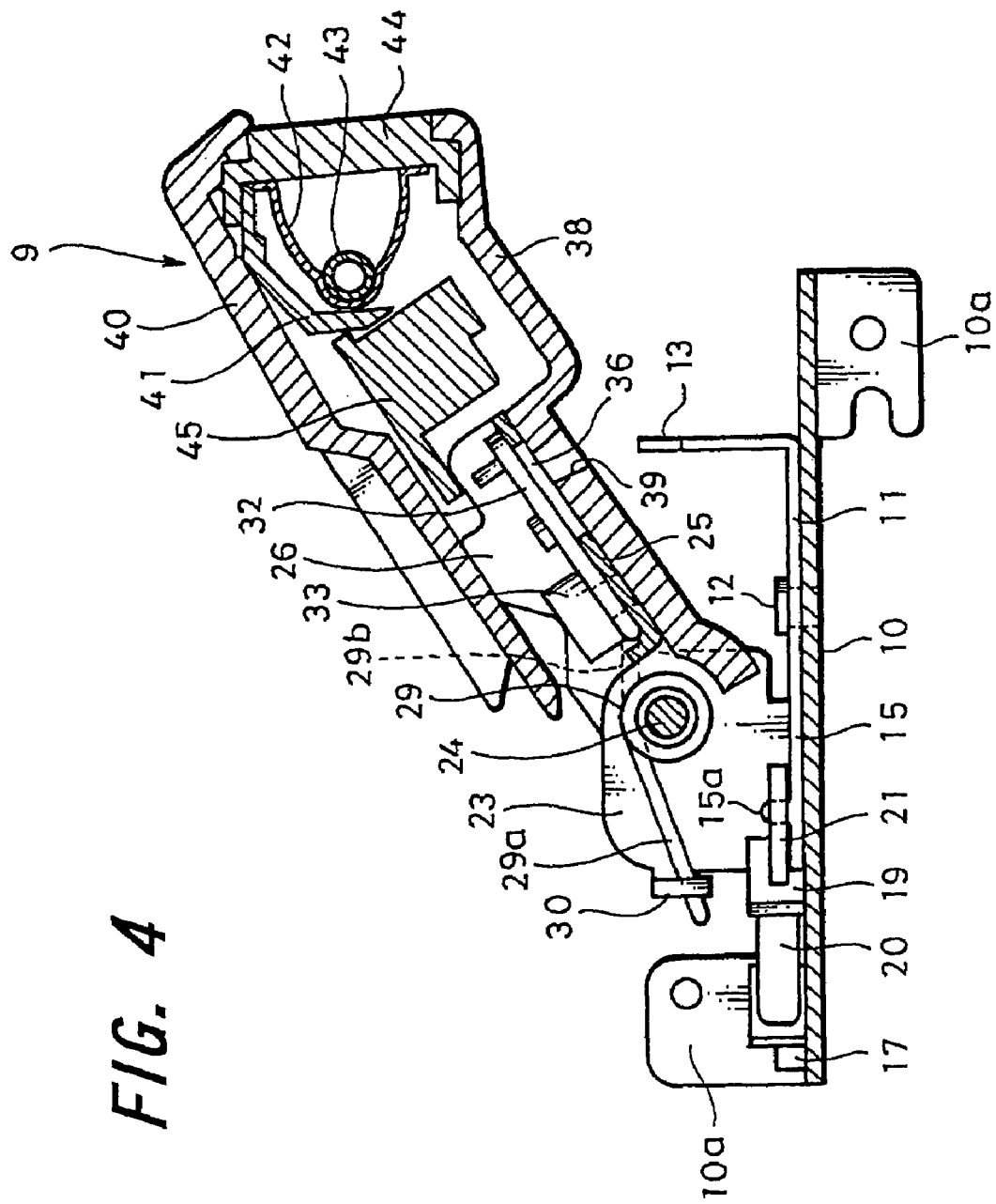

FIGS. 1 and 2 reproduce the fields of vision of the left eye; FIGS. 3 and 4 reproduce the field of vision of the right eye as perceived by one of the treated patients who suffered from glaucomatous neuropathy, respectively before treatment (FIGS. 1 and 3) and after treatment, 10 days later (FIGS. 2 and 4).

Figure 5:
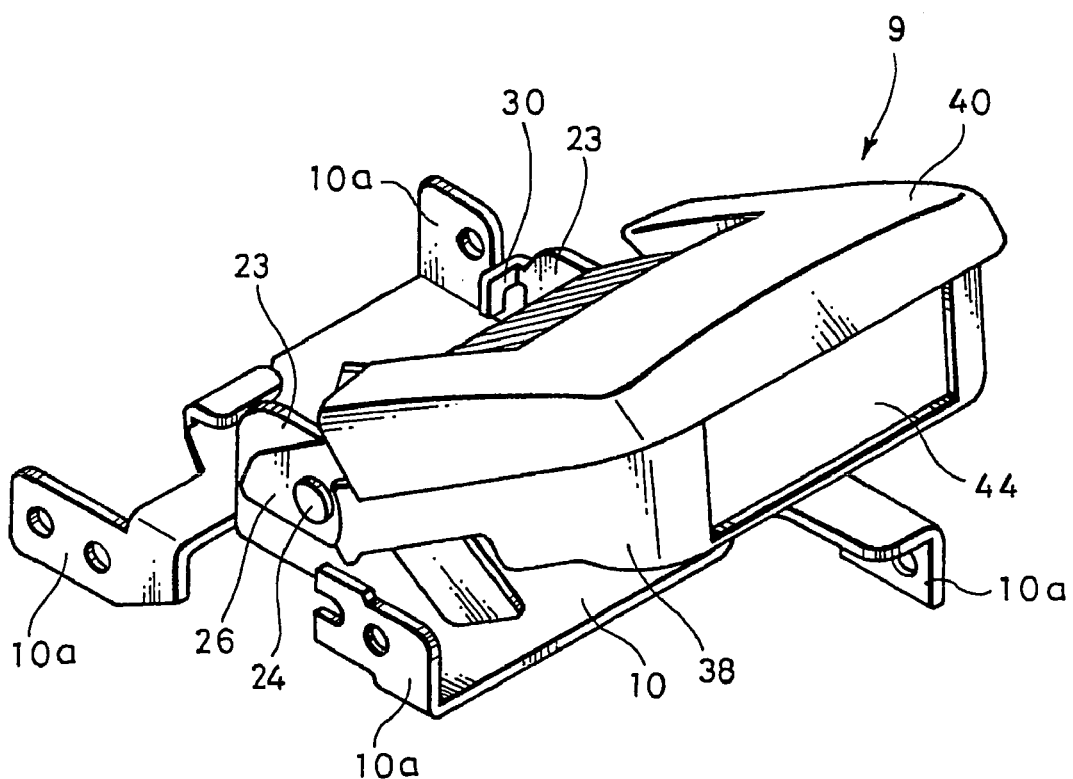
Figure 6:
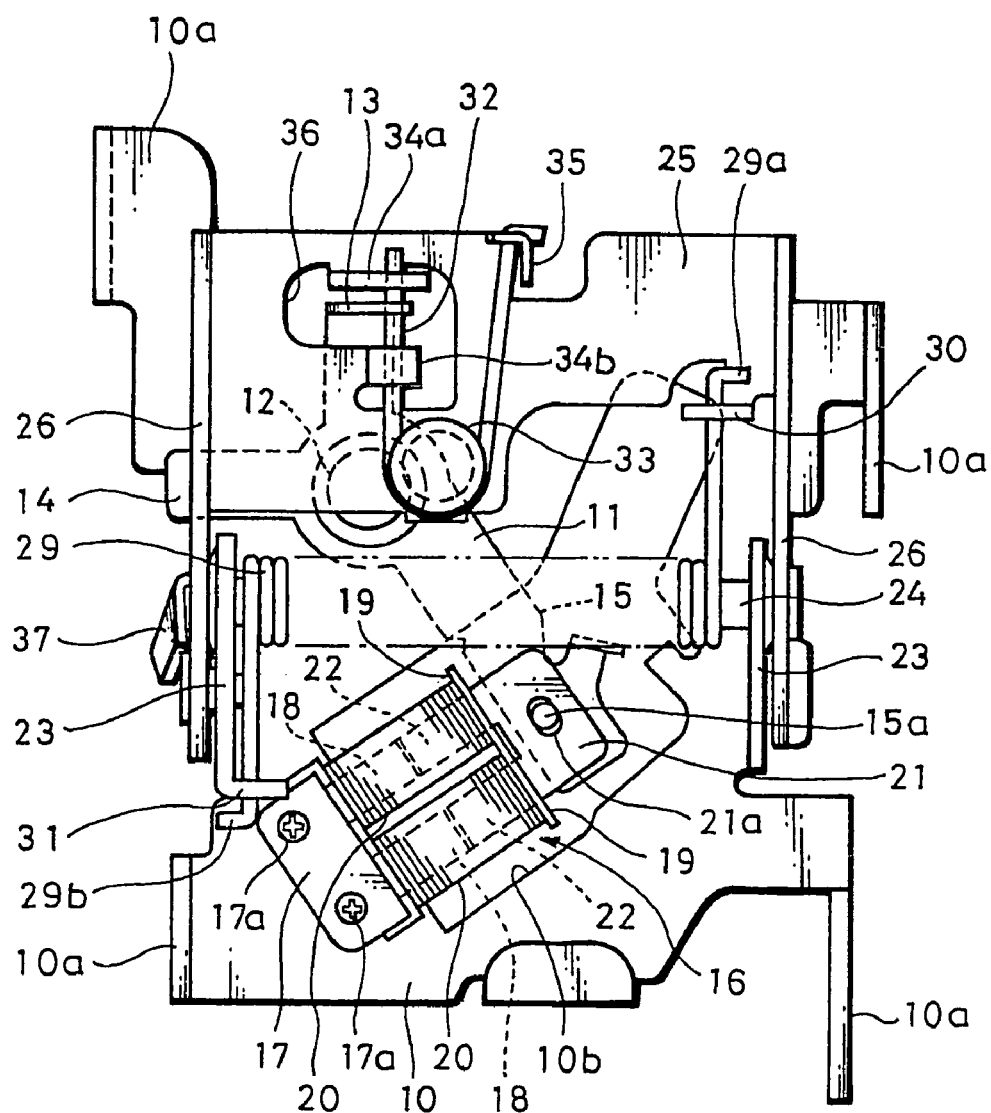
Figure 7:
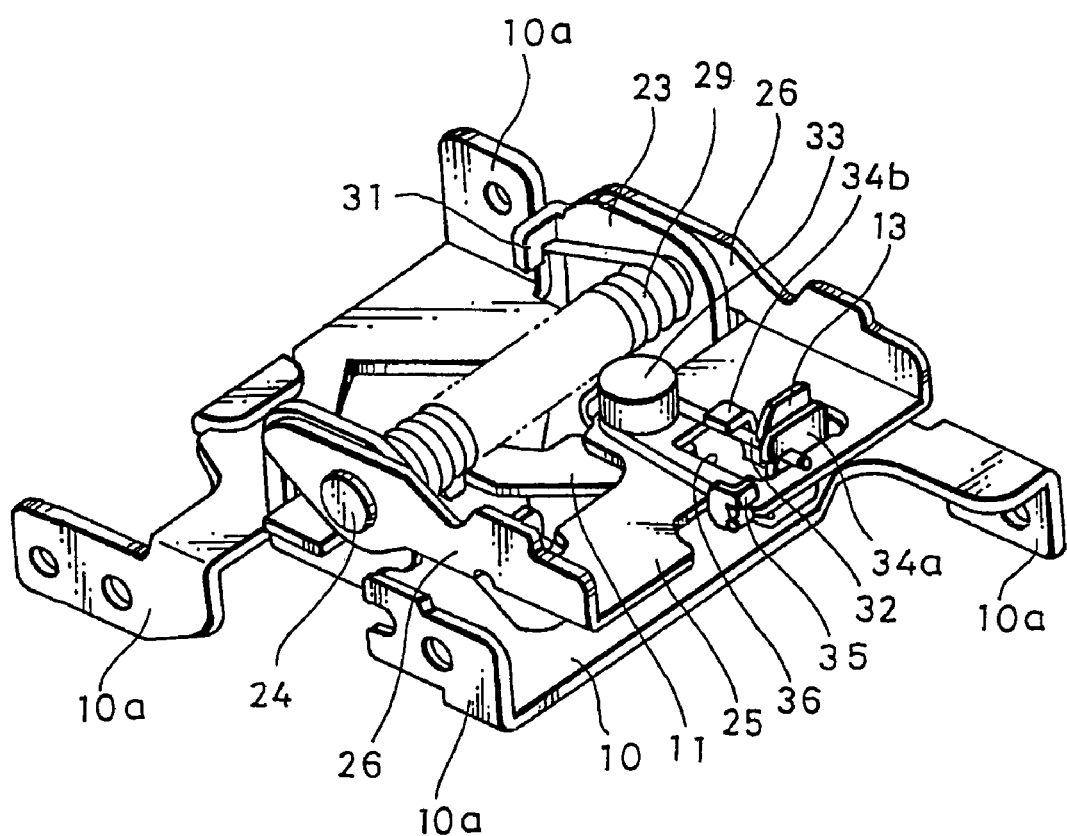
Figure 8:
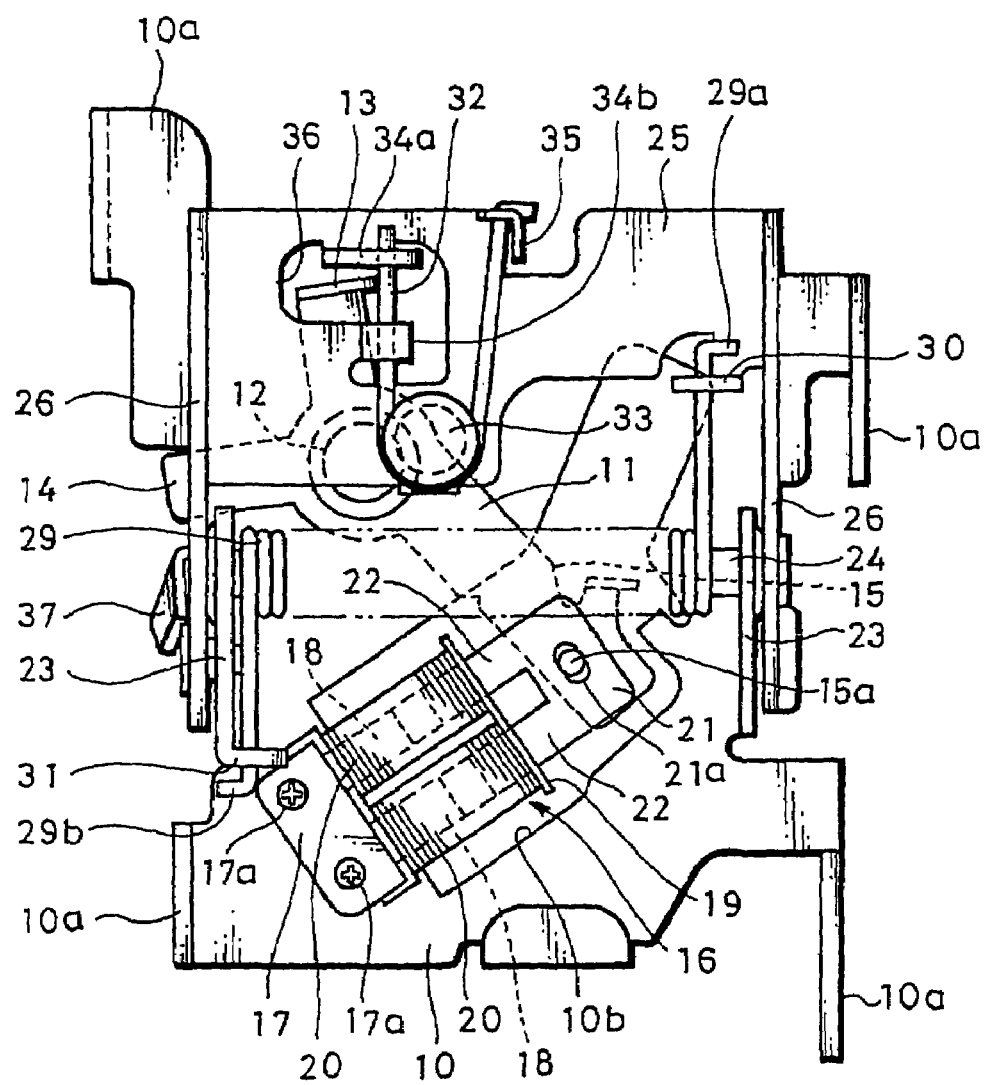
Figure 9:
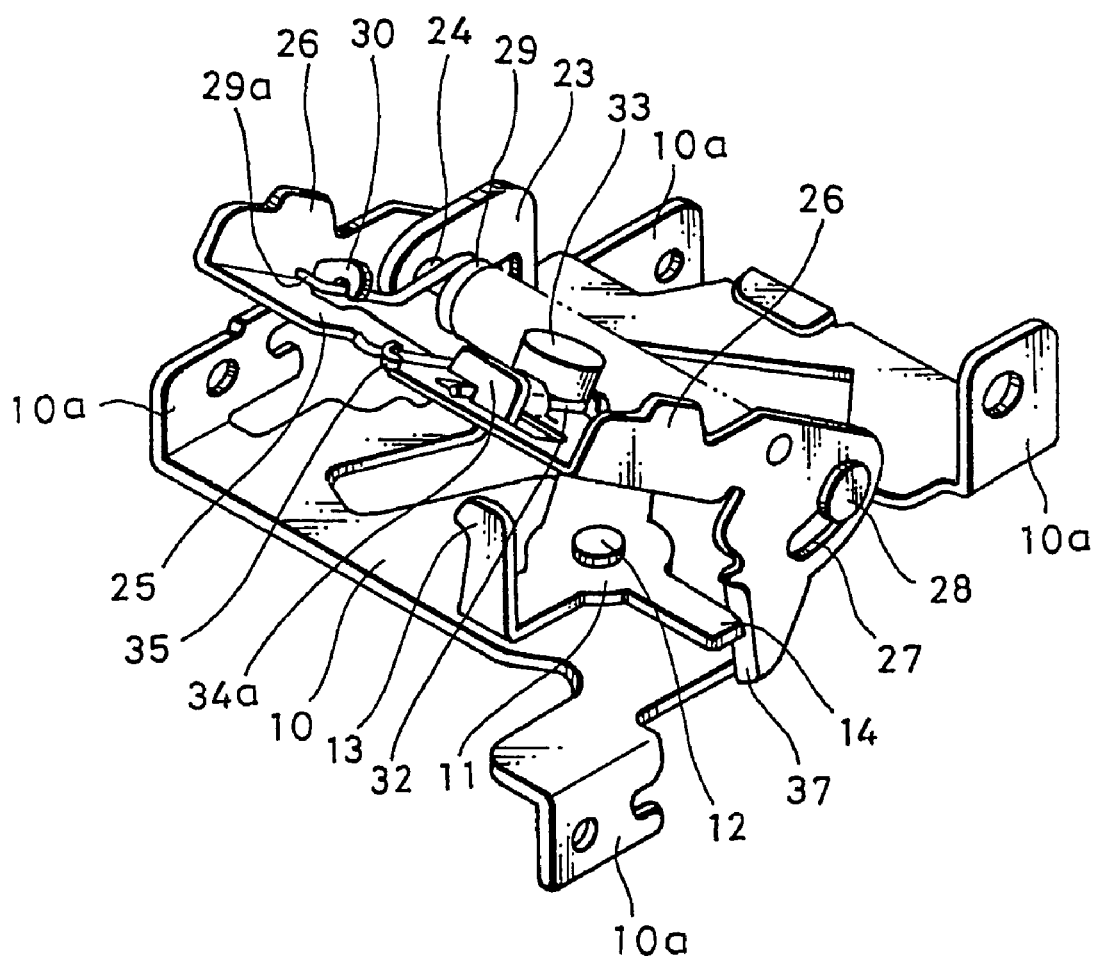
Figure 10:
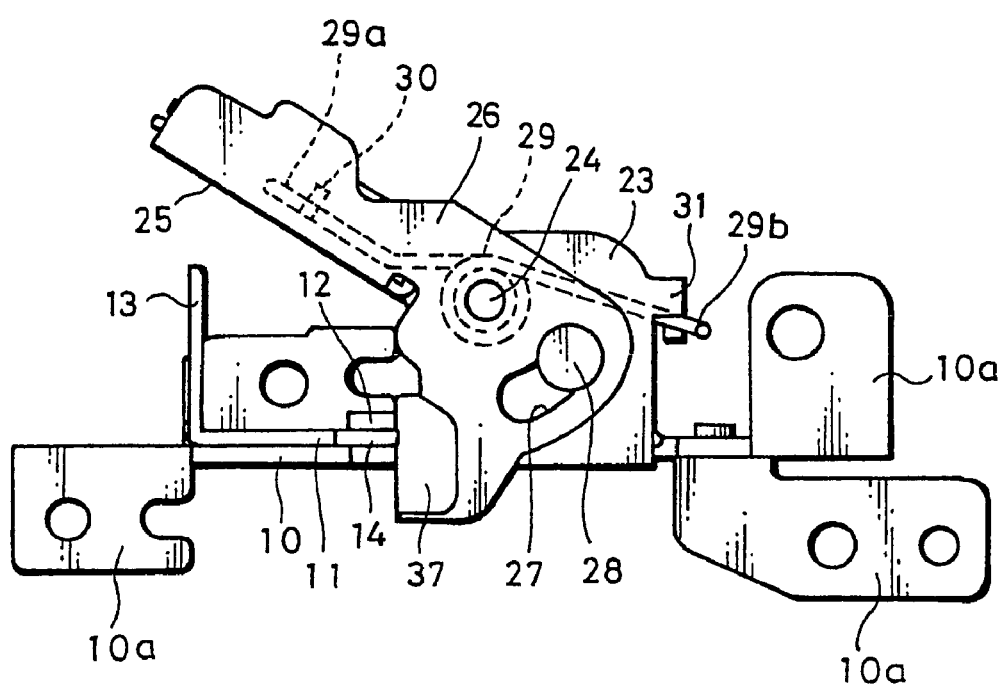
Figure 11:
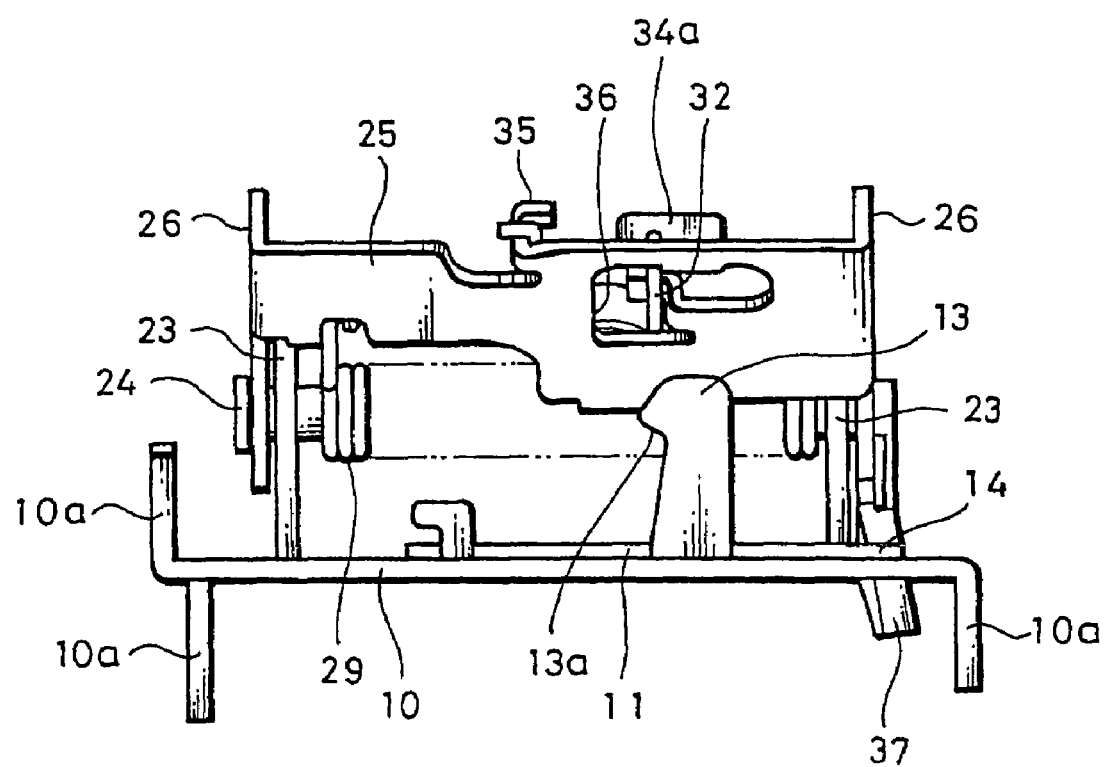
Figure 12:
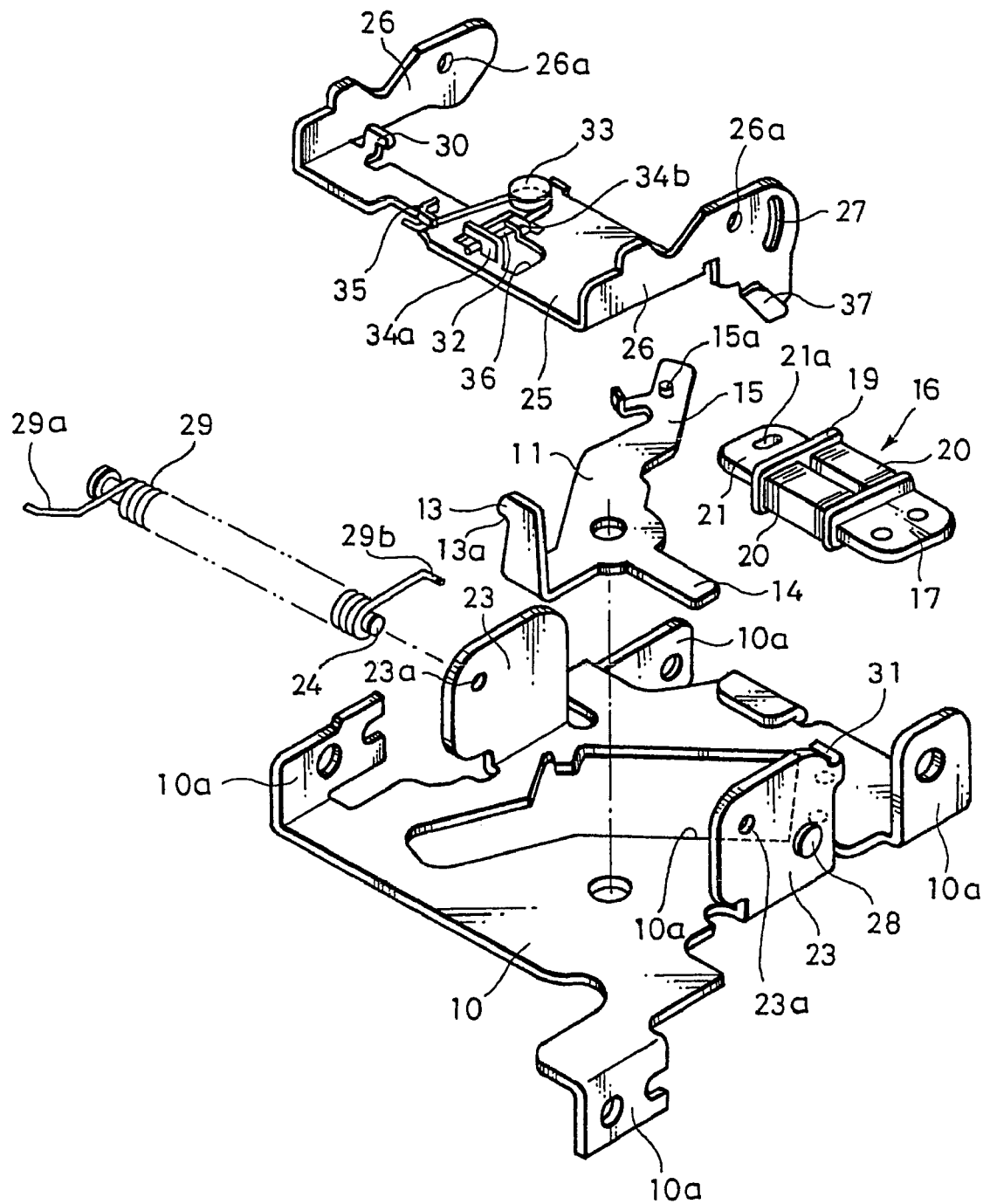
Figure 13:
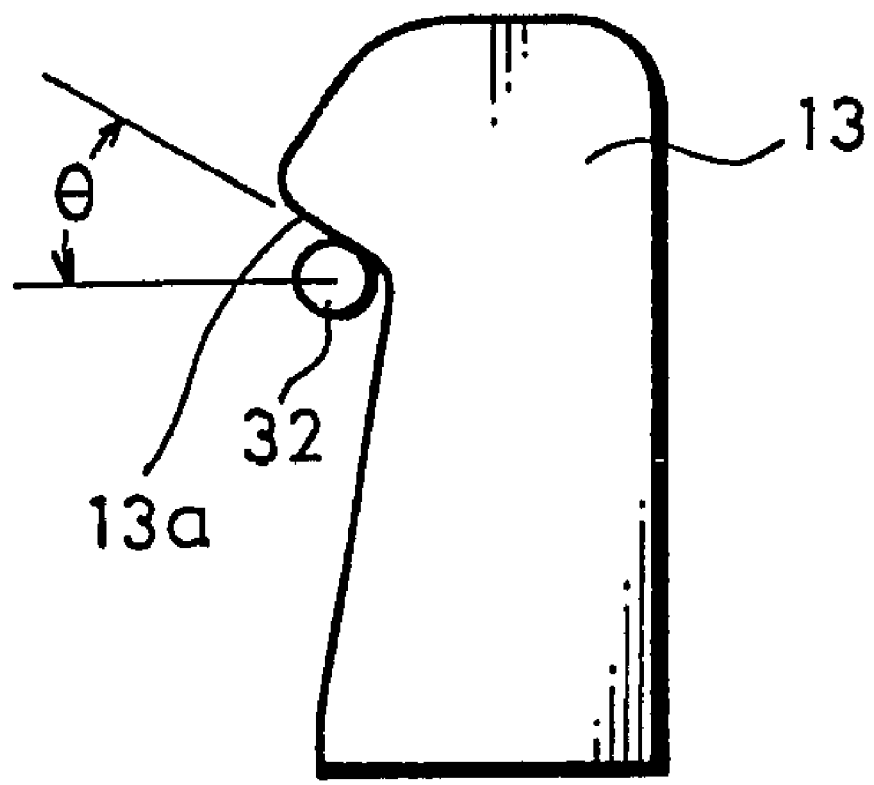
Figure 14:
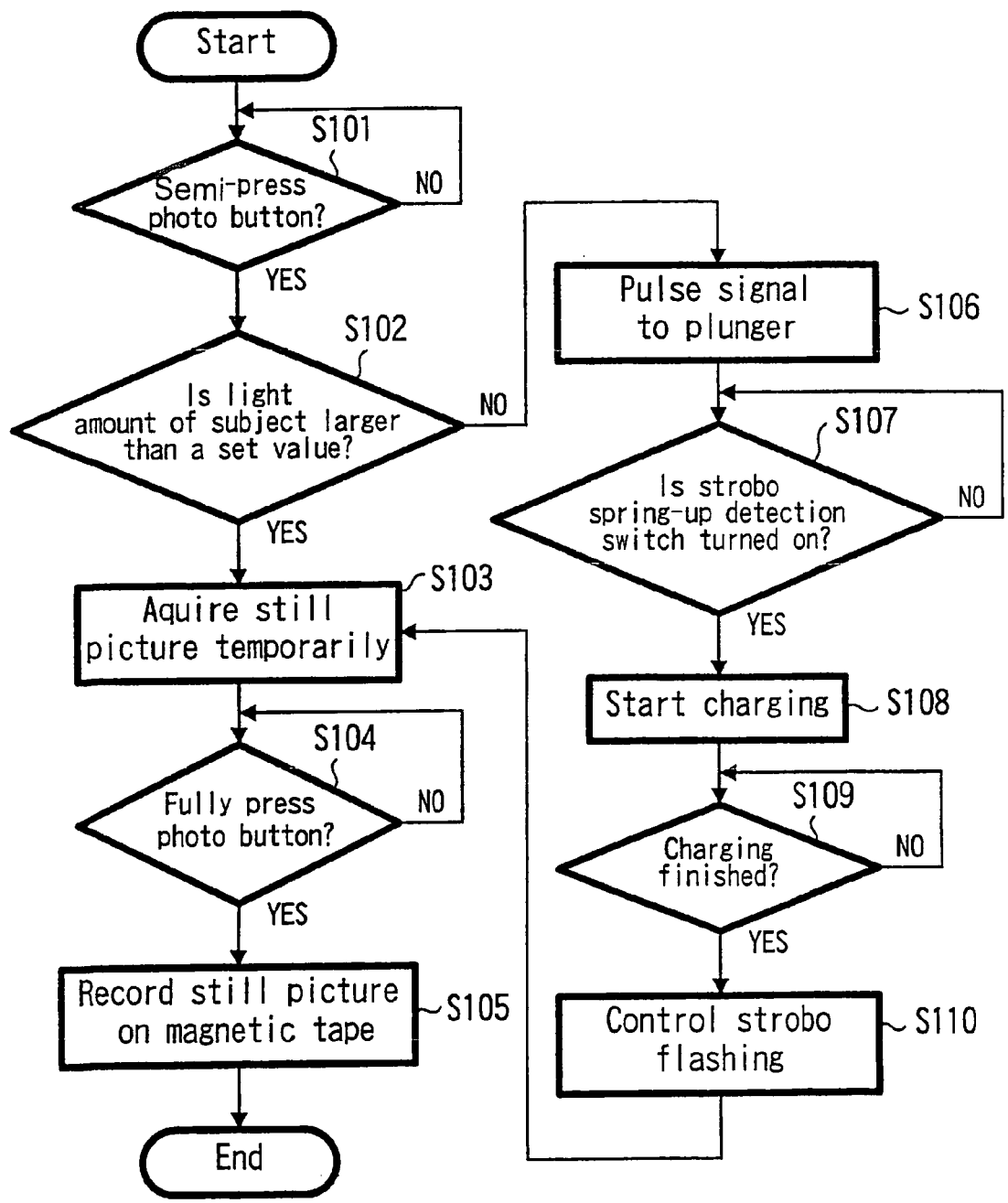
Figure 15:
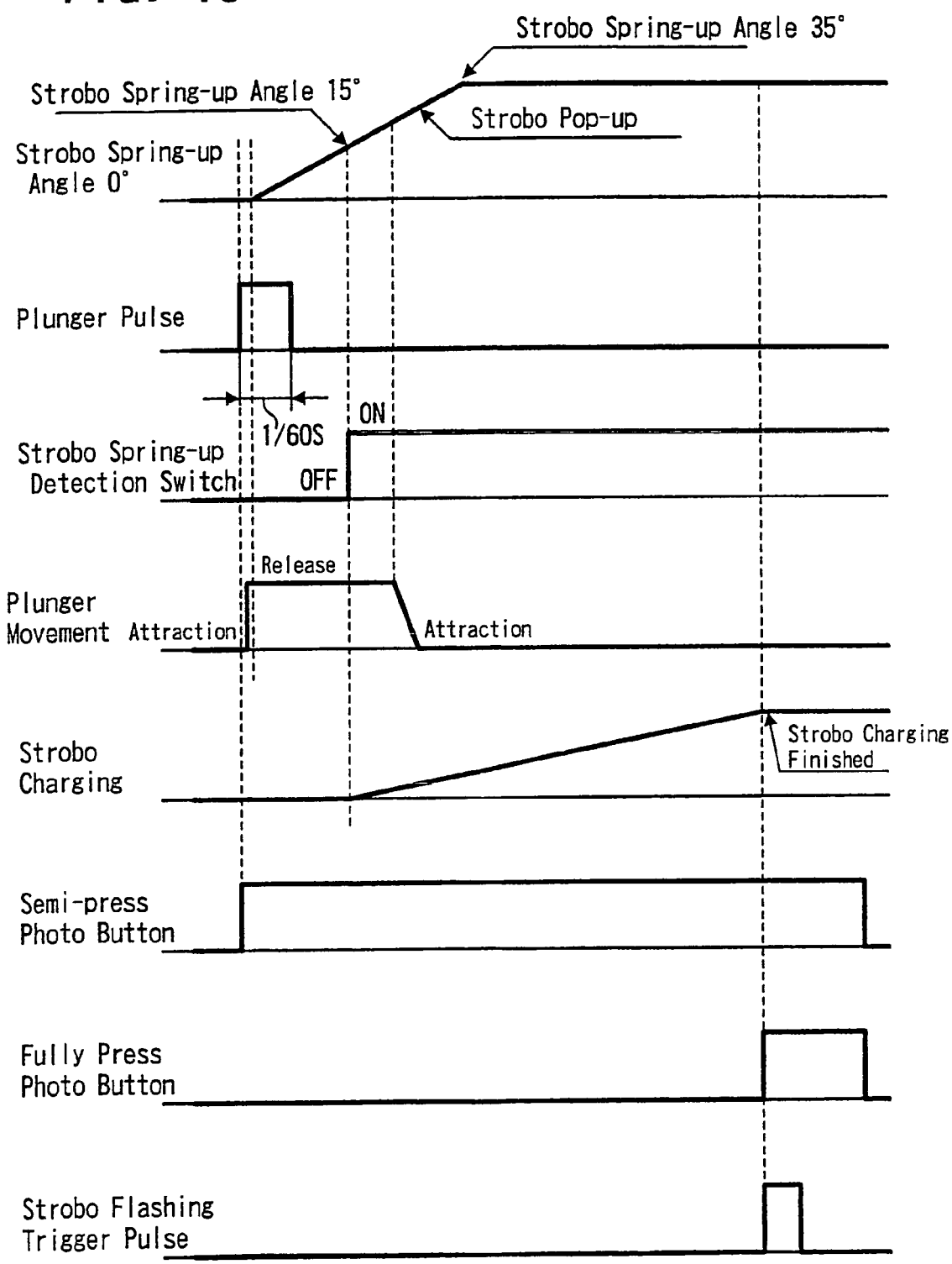
Figure 16:
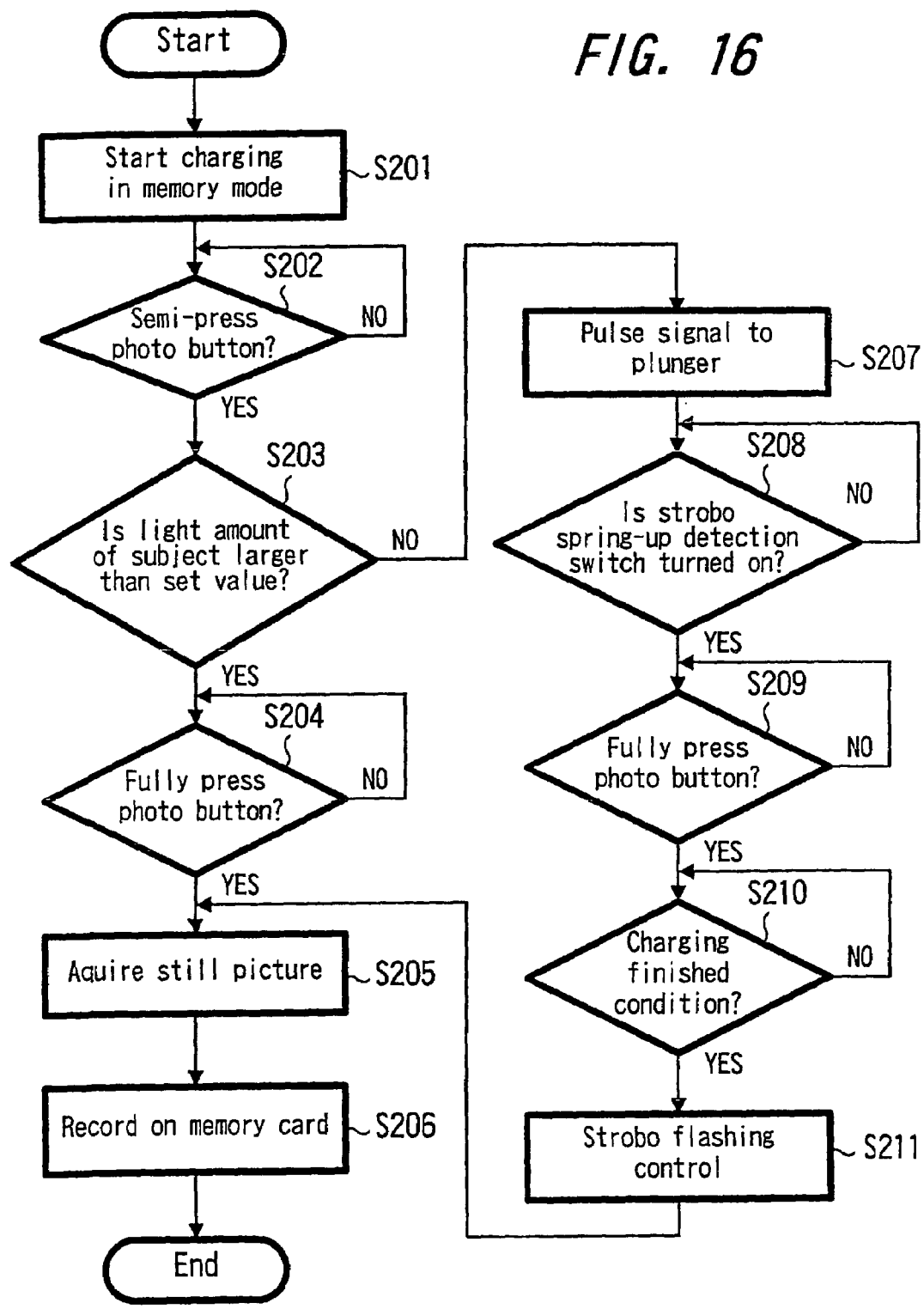
Figure 17:
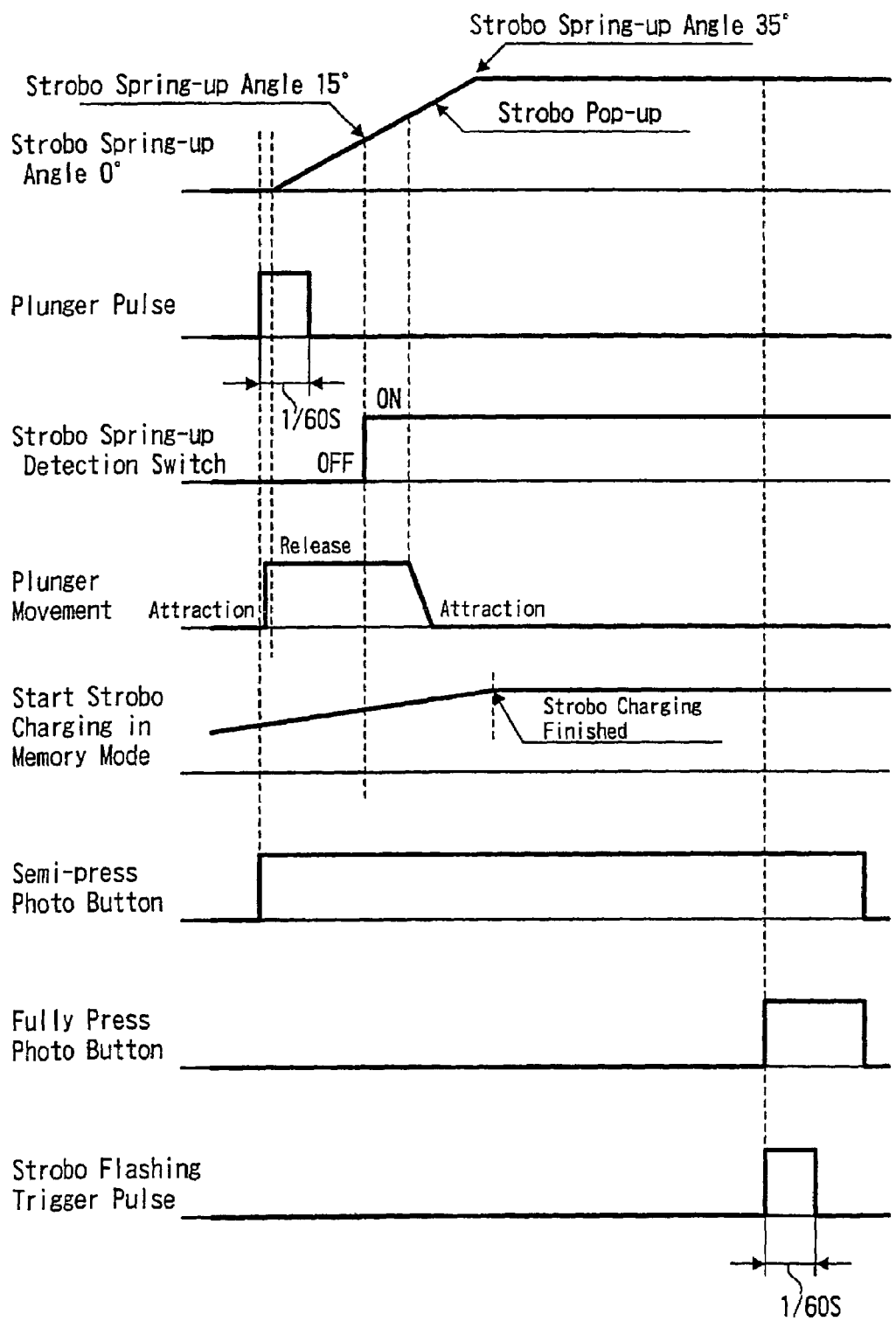

FIGS. 5 and 6 reproduce the fields of vision of the left eye; FIGS. 7 and 8 reproduce the field of vision of the right eye as perceived by one of the treated patients who suffered from sectorial retinitis pigmentosa, respectively before treatment (FIGS. 5 and 7) and after treatment, two months later (FIGS. 6 and 8).

The upper left portion of each of the Figures shows the grey scale (GS); the lower left portion shows the Bebie curve; the upper right portion shows the threshold values (in dB) measured at set points in the retina; and the lower right portion shows comparative values (in dB).

The grey scale provides an "image" of visual function, point by point, of different regions of the retina; the palest zones correspond to regions in which the visual functions are the least altered; the darkest zones correspond to those that have altered the most. A relative lightening of one of the regions in question after treatment demonstrates a local improvement in visual functions. A reduction in the darkest regions also indicates local visual recovery in regions that have become lighter.

The values that appear in the right hand portions of the figures correspond to the threshold values measured locally at set points in the retina. The increase in these values measured at certain points after treatment demonstrate a local improvement in vision. In contrast, the values that appear in the lower right hand portions of the figures correspond to local loss of vision in the zones concerned of the retina compared with the normal. A reduction in these values, when observed after treatment, is evidence of an improvement in visual function on a local level.

The Bebie curves also provide comparative images of the visual capacity of the subject under examination (lower curves) compared with the curves for normal or quasi-normal subjects (upper curves). An improvement in visual function in a treated patient is demonstrated when the Bebie curve comes close to the curves obtained for normal subjects.

Remarkably, equivalent observations were made in "normal" subjects, in particular ageing subjects, to whom the drug had been administered, these ageing subjects regaining the mean sensitivity they knew when they were much younger.

Further characteristics of the invention will become clear from the following clinical observations that are, of course, provided solely by way of illustration and do not in any way limit the scope of the invention.

Glaucomatous Neuropathy

The ischemic origin of glaucomatous neuropathy was suspected in the light of angiographic exploration.

Fluorescein angiography showed:

1) Opitic papilla:

either a delay in impregnation of glaucomatous papilla;

or absolute impregnation defects. These faults correlated with alterations in the field of vision.

2) Choroid:

Fluorescein angiography showed:

a delay in choroidal filling: in 100% of cases;

an irregularity in sector filling;

abnormal visibility of principal choroidal vessels.

3) Retina:

Longer retinal arterial period.

Patients with known glaucoma presenting with arterial hypertension had an improvement in visual acuity and their field of vision in a very short period, as soon as treatment was commenced. We shall now list the effects obtained:

Visual acuity: substantial improvement, the most spectacular case being that of a patient whose visual acuity increased from 3/10 to 10/10 (LE) and from 6/10 to 8/10 (RE);

Field of vision: Studied by Goldmann comparison, and in particular with automated perimetry; the improvement was substantial and spectacular; on average, the loss in mean sensitivity reduced by 30%, which is original and exceptional;

Ocular tension: Significant reduction, but of an irregular amount.

The entirely relative reduction in intraocular pressure does not explain the rapid and spectacular improvements in the field of vision. With ramipril, the loss in mean sensitivity with automated perimetry (optopus™) reduced by an average of 30%, and absolute scotomas became relative. If a rise in intraocular pressure constitutes an aggravating factor for glaucomatous neuropathy, this disorder appears to consist essentially of an ischemic vascular disease necessitating vascular treatment.

FIGS. 1 to 4 also demonstrate an improvement in the visual function, in particular under the conditions summarised above. The data given for these Figures also appears in the tables below (the numbers, of course, correspond to those in the figures):

TABLE 1

Left eye before treatment

|  |  |  | Normal | Phase 1 | Phase 2 | Mean |
|---|---|---|---|---|---|---|
| Mean sensitivity | MS |  |  | 16.9 | 17.3 | 16.5 |
| Mean drop | MD | [dB] | −2..2 | 9.5 | 9.4 | 9.9 |
| Loss variance | LV | [dB] | 0..6 | 26.8 | 29.3 |  |
| Corr. Loss variance | CLV | [dB]$^2$ | 0..4 |  |  | 22.4 |
| Short term fluctuation | SF | [dB]$^2$ | 0..2 |  |  | 2.7 |
| Reliability factor | RF | [%] |  |  |  | 4.9 |

TABLE 2

Left eye after treatment

|  |  |  | Normal | Phase 1 | Phase 2 | Mean |
|---|---|---|---|---|---|---|
| Mean sensitivity | MS |  |  | 20.0 | 20.0 | 20.2 |
| Mean drop | MD | [dB] | −2..2 | 5.7 | 6.8 | 6.2 |
| Loss variance | LV | [dB] | 0..6 | 16.8 | 26.5 |  |
| Corr. Loss variance | CLV | [dB]$^2$ | 0..4 |  |  | 13.1 |
| Short term fluctuation | SF | [dB]$^2$ | 0..2 |  |  | 3.0 |
| Reliability factor | RF | [%] |  |  |  | 5.0 |

TABLE 3

Right eye before treatment

|  |  |  | Normal | Phase 1 | Phase 2 | Mean |
|---|---|---|---|---|---|---|
| Mean sensitivity | MS |  |  | 17.4 | 17.4 | 16.9 |
| Mean drop | MD | [dB] | −2..2 | 9.0 | 9.3 | 9.5 |
| Loss variance | LV | [dB] | 0..6 | 28.6 | 21.0 |  |
| Corr. Loss variance | CLV | $[dB]^2$ | 0..4 |  |  | 21.8 |
| Short term fluctuation | SF | $[dB]^2$ | 0..2 |  |  | 3.0 |
| Reliability factor | RF | [%] |  |  |  | 2.3 |

TABLE 4

Right eye after treatment

|  |  |  | Normal | Phase 1 | Phase 2 | Mean |
|---|---|---|---|---|---|---|
| Mean sensitivity | MS |  |  | 22.2 | 21.9 | 21.6 |
| Mean drop | MD | [dB] | −2..2 | 4.1 | 4.7 | 4.8 |
| Loss variance | LV | [dB] | 0..6 | 17.2 | 10.4 |  |
| Corr. Loss variance | CLV | $[dB]^2$ | 0..4 |  |  | 13.1 |
| Short term fluctuation | SF | $[dB]^2$ | 0..2 |  |  | 2.6 |
| Reliability factor | RF | [%] |  |  |  | 2.3 |

The figures show a substantial improvement in visual function; the tables provide a complementary illustration, in particular as regards the mean sensitivity, which increased from 16.5 to 20.2 for the left eye, and from 16.9 to 21.6 for the right eye. Similarly, a substantial regression in mean loss of vision with respect to the normal should be noted: from 9.9 to 6.2 for the left eye and from 9.5 to 4.8 for the right eye.

Degenerative Chorio-Retinopathy in Severe Myopia

The hypothesis that there is a vascular factor in the genesis of choroidal lesions has been advanced because of the presence of vascular lesions in the choroid. Vascular occlusion first affects the choriocapillary, which is atrophic, then involves the medium vessels followed by the large vessels. Atrophy follows, and even disappearance of the choroid predominating at the posterior pole and at least partially conditioning retinal attack, which becomes atrophic. However, the retinal vessels participate in such atrophy. The improvement in corrected visual acuity does not currently appear ever to have been established in severely myopic patients affected by a degenerative chorioretinopathy.

Even in a low dose, ramipril always causes an improvement in corrected visual acuity despite the existence of extremely severe myopic choroidosis. By way of example, visual acuity changed respectively: from simple light perception (LP) to 1/20 for the monophtalmic eye; from 2/10 (RE) 1/10 (LE) to 5/10 (RE) and 5/10 (LE); from 1.5/10 to 3/10; from 1/20 (both eyes) to 2/10 (RE) and 1/10 (LE); from 1/10 (RE) and 1/10 (LE) to 6/10 (RE) and 3/10 (LE). Clearly, the term RE used here means "right eye" and the term LE used here means "left eye".

Age-Related Macular Degeneration (ARMD)

The ischemic nature of ARMD has been evoked on the basis of the following data.

Angiographic Data:

A recent study has shown a reduction in macular choroidal perfusion in 26 out of 100 patients presenting a ARMD.

Histological study:
This showed:
a progressive increase in intervascular tissue, which can shrink the lumen of the choriocapillary and associated arterioles;
a reduction in the number and diameter of choroidal capillaries;
a reduction in the number of medium choroidal vessels;
anomalies, in particular atrophy of the perifoveolar retinal capillary bed; it appears atrophic.

The majority of patients presenting an age-related macular degeneration with or without sub-retinal neovessels treated with ramipril experienced improved visual acuity. By way of example, visual acuity changed respectively from 0.16 to 0.3; 0.2 to 0.5; from 0.05 to 0.2 (right eye) and 0.05 to 0.15 (left eye); from 0.2 to 0.4 (right eye) and from 0.5 to 0.8 (left eye); from 0.6 to 1; from 0.4 to 0.6 (right eye) and from 0.2 to 0.5 (left eye).

Hereditary Dystrophy of the Retina and Pigmentary Epithelium

Retinitis pigmentosa:
This disorder corresponds to a dystrophy in the cones and rods. It is characterized by the appearance of night blindness in infancy or adolescence, a progressive contraction of the peripheral field of vision starting with an equatorial annular scotoma, and results in a substantial loss in visual acuity or even blindness by adulthood.

A vascular component has been demonstrated in this type of dystrophy. It is shown by clinical, angiographic and histological analysis:
1. Clinical: Reduction in the size of retinal vessels.
2. Angiography:
increase in retinal circulation period;
dilation of capillaries of the retina and optic papilla;
choroidal circulation delay.
3. Histopathology:
thickening, with hyalitis, of the retinal vessel walls;
partial obliteration of choriocapillary, which becomes atrophic.

Development and Prognosis

The prognosis is poor. It is marked by a constant progression in the disorder towards blindness. There is no known treatment.

The existence of this vascular factor has given rise to the idea of testing the drugs of the invention in hereditary dystrophies of the retina and the pigmentary epithelium.

Ramipril was used in the following three disorders: retinitis pigmentosa; Stargardt's disease, fundus flavimaculatus; adult pseudo-vitelliform dystrophy. In all cases, it caused an improvement in visual function.

Retinitis Pigmentosa

Three patients were treated with 1.25 mg of ramipril orally and their visual acuity improved in the space of two months:

First patient: Visual acuity for the right eye changed from doubtful light perception to 1/50 and for the left eye, from 1/50 to 1.6/10.

Second patient: Monophthalmic visual acuity changed from 2/10 to 5/10.

Third patient: Suffering from sectorial retinitis pigmentosa, his visual acuity changed from 1.6 to 6/10 in the right eye and from 1.6 to 4/10 in the left eye. The mean sensitivity for the automated optometric field of vision improved from 16.5 to 18 in the right eye and from 16.8 to 19.9 in the left eye.

The electroretinogram was substantially improved, especially in the red and in the left eye.

Stargardt's Flavimaculatus Disease

One patient was treated; acuity improved from 1/20 to 1/10 in the right eye and from 1/50 to 3/10 in the left eye.

Pseudovitelliform Dystrophy

One patient was tested. Acuity improved in one month from 1.6 to 2/10 in the right eye and from 2/10 to 3/10 in the left eye. The activity of the ramipril in these hereditary dystrophies is unique.

Reproductions of the fields of vision for the third patient with sectorial retinitis pigmentosa, respectively before and after two months of treatment, are shown by way of example in FIGS. 5 and 6 for the left eye, and in FIGS. 7 and 8 for the right eye.

FIGS. 5 to 8 also show a substantial improvement in visual function. The data shown in respectively corresponding Tables 5 to 8 provide a supplemental illustration. In particular, the mean sensitivity improved from 16.8 to 20.9 for the left eye and from 16.5 to 18.3 for the right eye. Similarly, the average loss of vision with respect to the normal dropped from 10.3 to 6.5 for the left eye and 10.6 to 8.8 for the right eye.

TABLE 5

Left eye before treatment

|  |  |  | Normal | Phase 1 | Phase 2 | Mean |
|---|---|---|---|---|---|---|
| Mean sensitivity | MS |  |  | 17.3 | 17.9 | 16.8 |
| Mean drop | MD | [dB] | −2..2 | 9.8 | 9.6 | 10.3 |
| Loss variance | LV | [dB] | 0..6 | 60.6 | 52.8 |  |
| Corr. Loss variance | CLV | $[dB]^2$ | 0..4 |  |  | 52.5 |
| Short term fluctuation | SF | $[dB]^2$ | 0..2 |  |  | 2.5 |
| Reliability factor | RF | [%] |  |  |  | 9.8 |

TABLE 6

Left eye after treatment

|  |  |  | Normal | Phase 1 | Phase 2 | Mean |
|---|---|---|---|---|---|---|
| Mean sensitivity | MS |  |  | 21.2 | 20.8 | 20.9 |
| Mean drop | MD | [dB] | −2..2 | 6.2 | 7.0 | 6.5 |
| Loss variance | LV | [dB] | 0..6 | 51.8 | 63.9 |  |
| Corr. Loss variance | CLV | $[dB]^2$ | 0..4 |  |  | 48.0 |
| Short term fluctuation | SF | $[dB]^2$ | 0..2 |  |  | 1.9 |
| Reliability factor | RF | [%] |  |  |  | 7.9 |

TABLE 7

Right eye before treatment

|  |  |  | Normal | Phase 1 | Phase 2 | Mean |
|---|---|---|---|---|---|---|
| Mean sensitivity | MS |  |  | 16.8 | 16.0 | 16.5 |
| Mean drop | MD | [dB] | −2..2 | 10.2 | 11.5 | 10.6 |
| Loss variance | LV | [dB] | 0..6 | 70.4 | 86.9 |  |
| Corr. Loss variance | CLV | $[dB]^2$ | 0..4 |  |  | 66.0 |
| Short term fluctuation | SF | $[dB]^2$ | 0..2 |  |  | 2.4 |
| Reliability factor | RF | [%] |  |  |  | 12.2 |

TABLE 8

Right eye after treatment

|  |  |  | Normal | Phase 1 | Phase 2 | Mean |
|---|---|---|---|---|---|---|
| Mean sensitivity | MS |  |  | 18.4 | 18.2 | 18.3 |
| Mean drop | MD | [dB] | −2..2 | 8.7 | 9.2 | 8.8 |
| Loss variance | LV | [dB] | 0..6 | 67.5 | 79.8 |  |
| Corr. Loss variance | CLV | $[dB]^2$ | 0..4 |  |  | 65.6 |
| Short term fluctuation | SF | $[dB]^2$ | 0..2 |  |  | 1.7 |
| Reliability factor | RF | [%] |  |  |  | 10.3 |

Retinal Venous Occlusions

The syndrome of occlusion of the central vein of the retina or one of its branches corresponds to a slowing down of the circulation to a greater or lesser extent. It does not stop completely.

It is defined by the presence of fundamental symptoms:
alteration in vision;
retinal circulatory slowdown;
venous dilation;
retinal haemorrhages;
diffuse retinal oedema;
cotton-like nodules;
alteration of capillary bed.

The prognosis for this type of disorder is uncertain. It depends on the ciinical form. Complications can aggravate the situation, in particular macular oedema, haemorrhage of the aqueous humour and neovascular glaucoma.

The only known treatment is laser photocoagulation. This treats the complications rather than the occlusion itself.

The majority of patients treated with ramipril improved both on the functional and on the angiographic level.

By way of example, two patients presenting an oedematous and ischemic type venous branch occlusion had improved visual acuity of respectively 2/10 to 8/10 and 6/10 to 10/10 in the space of two months.

By improving the perfusion pressure, ramipril improves blood flow and thus directly treats venous occlusion, which is once again defined as a slowing down of the venous circulation.

Retinal Epitheliopathy and Central Serous Chorioretinopathy (CSCR)

Vascular alterations have been proved. Indocyanine green angiography has shown these diffuse choroidal vascular alterations with choroidal hyperpermeability.

This latter causes serous detachment of the pigmentary epithelium. The pressure exerted on the pigmentary epithelium produces a leak that mechanically causes macular retinal serous detachment.

In the space of a few days to a few weeks, the use of ramipril has caused a reduction in the blister and thus application of the retinal neuroepithelium: this leads to an improvement in visual acuity and in the central field of vision.

For ramipril and ramiprilat, the improvement in field of vision is brought about by doses that do not cause arterial hypertension in the healthy subject.

Taking the vasodilatory action of ramipril and ramiprilat into account and because of the responsibility of the vascular factor in the development of the six pathologies, namely glaucomatous neuropathy, degenerative chorioretinopathy of severe myopia, ARMD, central serous chorioretinopathy, retinal venous occlusion and hereditary dystrophies of the retina, it can be seen that these substances can only have an effect in all other chorioretinal disorders involving a vascular component.

The invention is not limited to the use of ramipril and ramiprilat for the treatment of the disorders mentioned above. Other angiotensin converting enzyme inhibitors can be substituted that can induce effects 1, 2 and 3 mentioned above, in doses that are sufficiently low not to affect the general pressure in persons to whom it will be administered to those ends, in particular if the inhibitors have respective inhibition and isomerisation reversibility reaction constants satisfying the criteria defined above.

The term "visual function" as used in the claims below should be understood to refer more particularly but not in a limiting manner to visual acuity or to the field of vision or, as is preferable, to both at once.

The invention thus concerns a neuroprotective and retinoprotective ophtalmologic drug that can interrupt the process of degradation of visual function and even reverse its course, characterized in that its active principle is constituted by an inhibitor for the enzyme converting angiotensin 1 to angiotensin 2 with a high degree of stability, and moreover the inhibitor simultaneously has:

an equilibrium inhibition constant $K_1$ that governs the in vitro inhibition of rabbit converting enzyme by the inhibitor, the constant being lower than that of enalaprilat (50 pmol/l); and a constant $k_4$ for the reversible isomerisation of the enzyme-inhibitor complex formed, the constant being lower than that of the complex formed by enalaprilat and the converting enzyme $(1.1 \times 10^{-4})(S1)$ in a medium (50 mM/l Hepes, 300 mmol/l NaCl, 1 micromol/l $ZnCl_2$, pH 7.5), wherein the vasodilatory activity is manifest not only in the arteries but also in the veins.

Preferably, the drug of the invention is more lipophilic in nature than enalaprilat.

The invention also concerns a drug in which ramipril or ramiprilat is in the form of their pharmaceutically acceptable salts or any other derivative of ramiprilat that can liberate ramiprilat into the organism to which the active principle is administered.

What is claimed is:

1. A method for maintaining or improving the visual acuity and the field of vision in a patient in need of such treatment, said method comprising:
administering a drug comprising ramipril, wherein said drug maintains or improves visual acuity and the field of vision.

2. The method according to claim 1, wherein said drug is an ophthalmic neuro-protector and/or a retinoprotector.

3. The method according to claim 1, wherein said drug is administered orally.

4. The method according to claim 3, wherein ramipril is administered at a dose of 0.5 to 5 mg/day.

5. The method according to claim 3, wherein ramipril is administered at a dose of 1 to 2 mg/day.

6. The method according to claim 3, wherein ramipril is administered at a dose of 1.25 mg/day.

7. The method according to claim 1, wherein said drug is administered parenterally.

8. The method according to claim 7, wherein said drug is administered intravenously or intramuscularly or transdermically or topically.

9. The method according to claim 8, wherein said drug is administered topically to the eye.

10. The method according to claim 9, wherein said drug is administered as an ophthalmic solution.

11. The method according to claim 1, wherein said patient has a degenerating chorioretinopathy or has an optic neuropathy or has both a degenerating chorioretinopathy and an optic neuropathy.

12. The method according to claim 1, wherein said patient has a glaucomatous neuropathy.

13. The method according to claim 1, wherein said patient has a degenerative chorioretinopathy in severe myopia.

14. The method according to claim 1, wherein said patient has age-related macular degeneration with or without subretinal neovessels.

15. The method according to claim 1, wherein said patient has a central serous chorioretinopathy or a chronic central serous chorioretinopathy.

16. The method according to claim 1, wherein said patient has a hereditary dystrophy of the retina.

17. The method according to claim 16, wherein said hereditary dystrophy of the retina is a retinitis pigmentosa.

18. The method according to claim 1, wherein said patient has a retinal venous occlusion.

19. The method according to claim 1, wherein said patient is 60 years or older.

* * * * *